United States Patent [19]
Smith et al.

[11] Patent Number: 5,250,035
[45] Date of Patent: Oct. 5, 1993

[54] CANNULA AND STYLET SYSTEM

[75] Inventors: Gary N. Smith, Libertyville; Donald H. Patrick, Gurnee, both of Ill.

[73] Assignee: Abbott Laboratories, Abbott Park, Ill.

[21] Appl. No.: 871,559

[22] Filed: Apr. 20, 1992

[51] Int. Cl.$^5$ .......................................... A61M 5/178
[52] U.S. Cl. .................................. 604/164; 604/168; 604/900
[58] Field of Search ................ 604/491, 51, 53, 158, 604/164, 165, 166, 168, 170, 174, 274, 900; 606/185; 128/753, 754

[56] References Cited

U.S. PATENT DOCUMENTS

| | | | |
|---|---|---|---|
| 3,352,306 | 11/1967 | Hirsch | 604/168 |
| 4,609,370 | 9/1986 | Morrison | 604/165 |
| 4,817,631 | 4/1989 | Schnepp-Pesch et al. | 128/753 |
| 4,861,334 | 8/1989 | Nawaz | 604/164 |
| 4,973,312 | 11/1990 | Andrew | 604/158 |
| 5,006,122 | 4/1991 | Wyatt et al. | 604/158 |
| 5,135,525 | 8/1992 | Biscoping et al. | 604/166 |

FOREIGN PATENT DOCUMENTS

| | | | |
|---|---|---|---|
| 4020956 | 1/1991 | Fed. Rep. of Germany | 606/185 |
| 9108785 | 6/1991 | World Int. Prop. O. | 604/158 |

Primary Examiner—John D. Yasko
Assistant Examiner—Anthony Gutowski
Attorney, Agent, or Firm—Thomas M. Breininger

[57] ABSTRACT

A needle system including a plastic cannula and a stylet, and a procedure utilizing the needle system for positioning the end of a spinal catheter within the subarachnoid space surrounding a patient's spinal cord for continuous administration of anesthetics and/or analgesic medications. The stylet has a pencil-point sharpened end for forming a minimal size opening in the dura defining the subarachnoid space to minimize the loss of cerebrospinal fluid therefrom during this procedure. The cannula has a hub formed of glass-clear plastic, which is provided with viewing recesses.

2 Claims, 3 Drawing Sheets

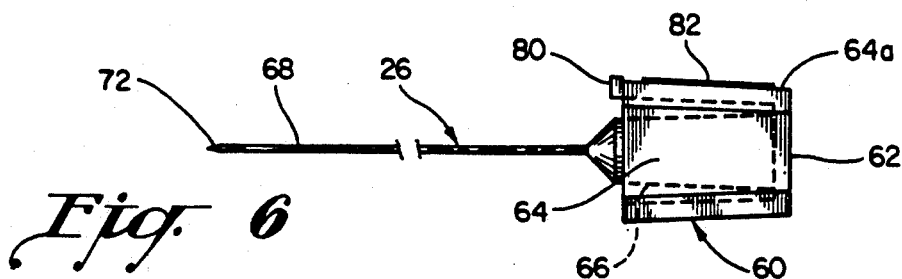
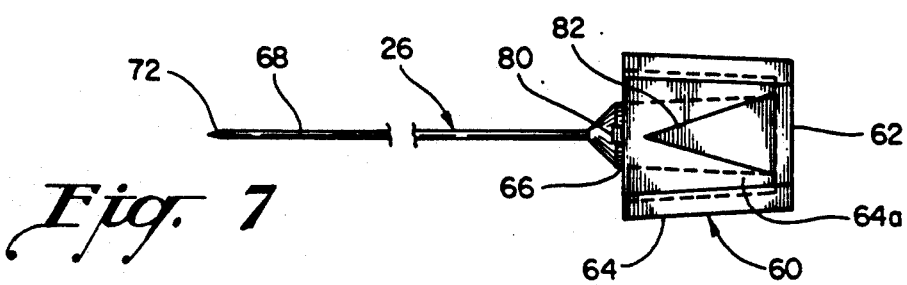
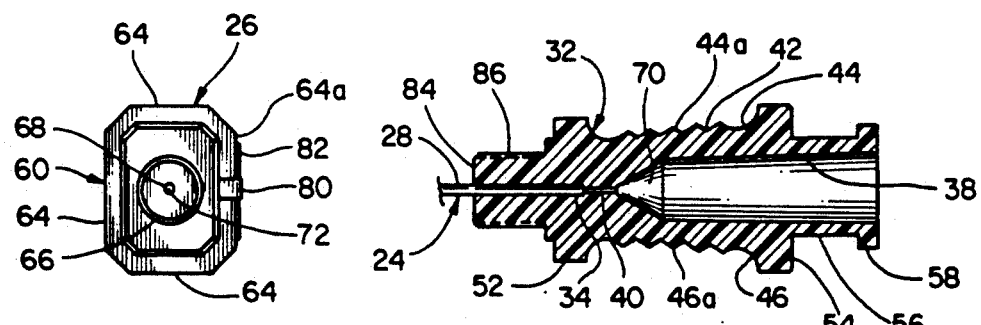
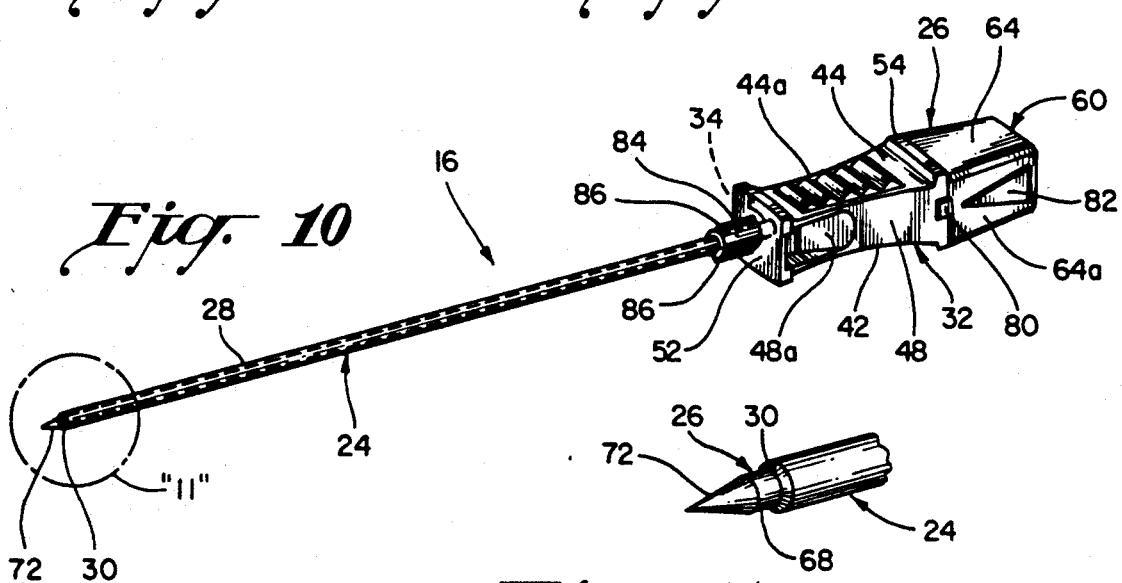

CANNULA AND STYLET SYSTEM

BACKGROUND OF THE INVENTION

Administering anesthetics and/or analgesic medications into the spinal canal through the dura of the spinal cord has to be done very carefully so as to minimize the loss of cerebrospinal fluid from the subarachnoid space which surrounds the spinal cord through such administration openings made in the dura. The loss of the cerebrospinal fluid produces such extremely severe spinal headaches in patients having this anesthetic procedure that, in certain cases, the patient must be maintained in a horizontal position so as to endure same. When such anesthetics, etc. are administered by means of spinal needles it may be necessary for multiple punctures to be made in a patient's dura which obviously increases the likelihood of a further loss of cerebrospinal fluid with each puncture. Further, such spinal needles quite commonly have a chisel-shaped point whereby the fibers of the dura are severed during the puncture procedure which requires a healing period before the puncture wound is fully closed to seal off the escape of further cerebrospinal fluid.

SUMMARY OF THE INVENTION

The present invention is directed to a new and improved needle system and procedure by means of which a spinal catheter may be introduced into the subarachnoid space surrounding the spinal cord with a minimal loss of cerebrospinal fluid through the dura. With this arrangement, anesthetics and/or analgesic medications may be administered to a patient at intervals as desired without the necessity of making separate punctures through the dura each time.

This needle system is characterized by a cannula, preferably formed of a plastic such as Teflon, which has a non-pointed but beveled distal end and a clear-plastic hub on its proximal end, the hub being provided with a through bore which is axially aligned with the bore of the cannula. The needle system of the present invention is further characterized by a stainless steel stylet which is insertable into the cannula and which has a plastic handle on its proximal end which interfits with the hub of the cannula so that, when so assembled, just a dura-piercing tip or point at the distal end of the stylet projects beyond the non-pointed distal end of the cannula. It is noted that the dura-piercing tip of the stylet is cone-shaped or pencil-point shaped whereby in piercing the dura the fibers thereof are gently spread apart rather than severed, as with chisel-shaped points, whereby to minimize the size and trauma of the opening therein. Further, this type of puncture wound heals much faster than one in which the tissue fibers have been severed. After a minimal size opening has been made in the dura with just the tips of the stylet and the cannula extending therethrough into the subarachnoid space surrounding the spinal cord, the stylet is removed from the cannula and a spinal catheter is passed therethrough into the subarachnoid space, after which the cannula is removed and the spinal catheter anchored down.

The present invention is directed to a new and improved needle system and procedure for administering anesthetics or analgesics to a patient in a manner such that there is a minimal loss of cerebrospinal fluid and thus a lessening of extremely painful spinal headaches.

An object of the present invention is to provide such a new and improved needle system which is characterized by a plastic cannula having a beveled distal end with a bored hub on its proximal end and a stainless steel stylet having a cone-shaped or pencil-point distal end and a handle on its proximal end which is engageable with the cannula hub when the stylet is inserted therein so that only the pencil-point distal end projects beyond the beveled end of the cannula whereby a minimal size opening is formed in the dura of the spinal cord whereby a spinal catheter may be introduced into the subarachnoid space surrounding the spinal cord upon removal of the stylet from the cannula.

A further object of the present invention is to provide such a new and improved needle system wherein the interengageable means between the cannula and the stylet is a notch provided in the cannula hub and a tab provided on the stylet handle.

Additional objects and advantages of the present invention will become apparent to one skilled in the art from the following detailed description.

BRIEF DESCRIPTION OF THE DRAWINGS

FIG. 6 is a top plan view of the stylet of applicants' new and improved needle system shown in FIG. 1;

FIG. 7 is a front elevational view of the stylet shown in FIG. 6;

FIG. 8 is a left end elevational view of the stylet as shown in FIG. 7;

FIG. 9 is a longitudinal sectional view taken generally along line 9—9 of FIG. 5;

FIG. 10 is a perspective view of a preferred embodiment of applicants' new and improved needle system;

FIG. 11 is an enlarged partial perspective view of the distal ends of the assembled cannula and stylet of applicants' needle system, the enlarged portion being circled with broken line in FIG. 10;

DESCRIPTION OF THE PREFERRED EMBODIMENT

Figure 1:
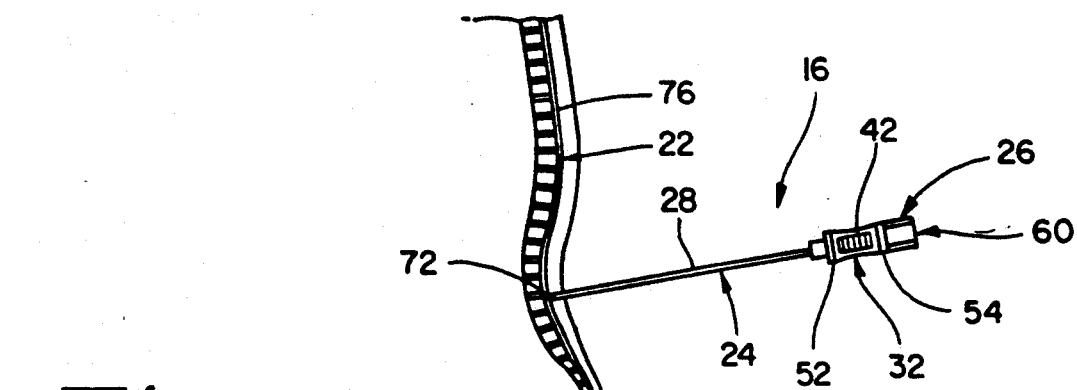
FIG. 1 is a diagrammatic view of a patient's back and spinal column and applicants' new and improved needle system for administering anesthetics and/or analgesics to the patient.
Figure 2:
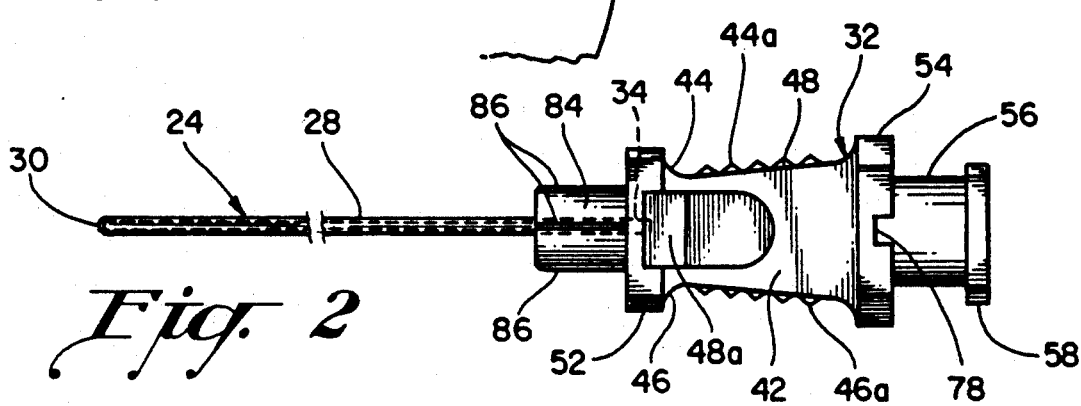
FIG. 2 is a front elevational view of the cannula of applicants' new and improved needle system shown in FIG. 1.
Figure 3:
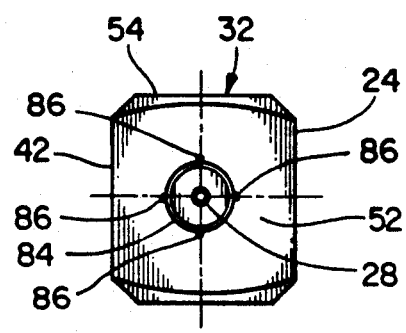
FIG. 3 is a left end elevational view of the cannula shown in FIG. 2.
Figure 4:
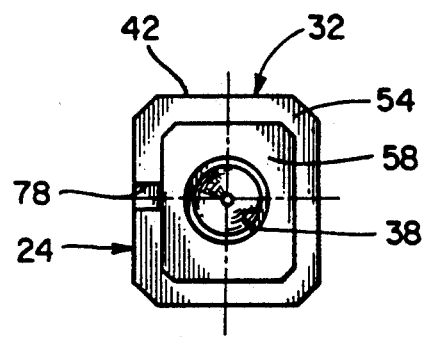
FIG. 4 is a right end elevational view of the cannula shown in FIG. 2.
Figure 5:
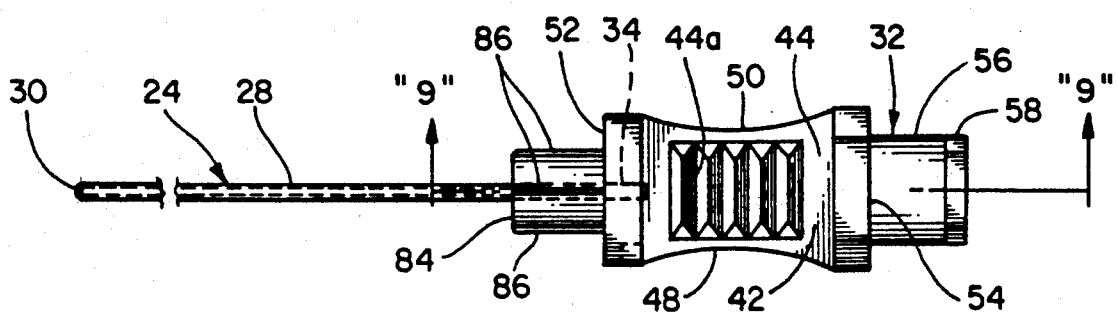
FIG. 5 is a top plan view of the cannula shown in FIG. 2.

Referring now to the drawings, a preferred embodiment of a new and improved needle system 16 of the invention is shown in FIGS. 2-11 with a preferred embodiment of a new and improved procedure of the invention for introducing a spinal catheter 18 into a subarachnoid space 20 which surrounds a patient's spinal cord 22, utilizing the new and improved needle system 16, being shown in FIGS. 1 and 12-14.

Figure 12:
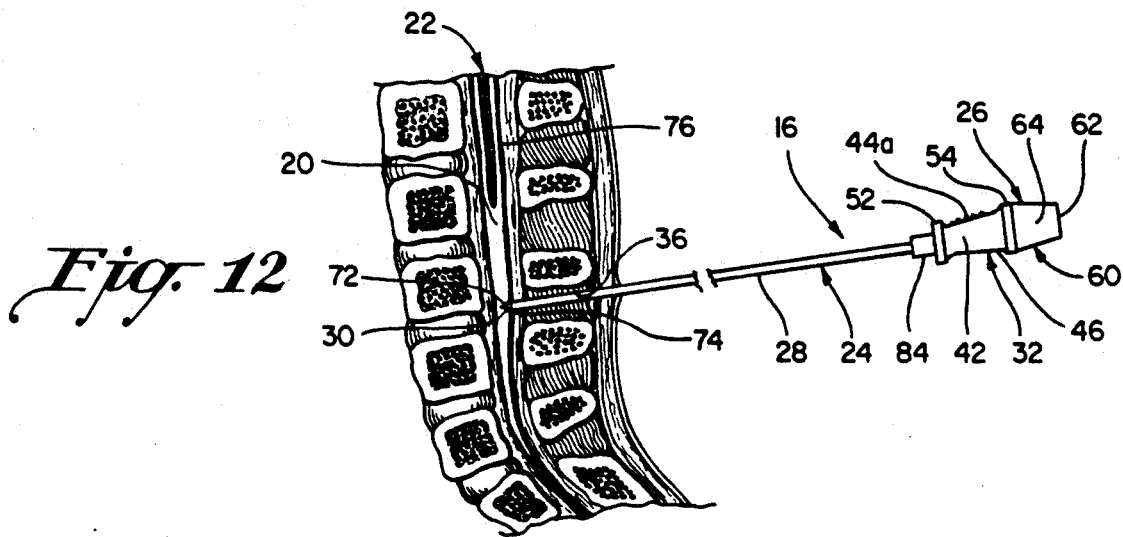
FIG. 12 is a diagrammatic view illustrating the use of applicants' new and improved needle system in forming a catheter opening in a patient's dura.
Figure 13:
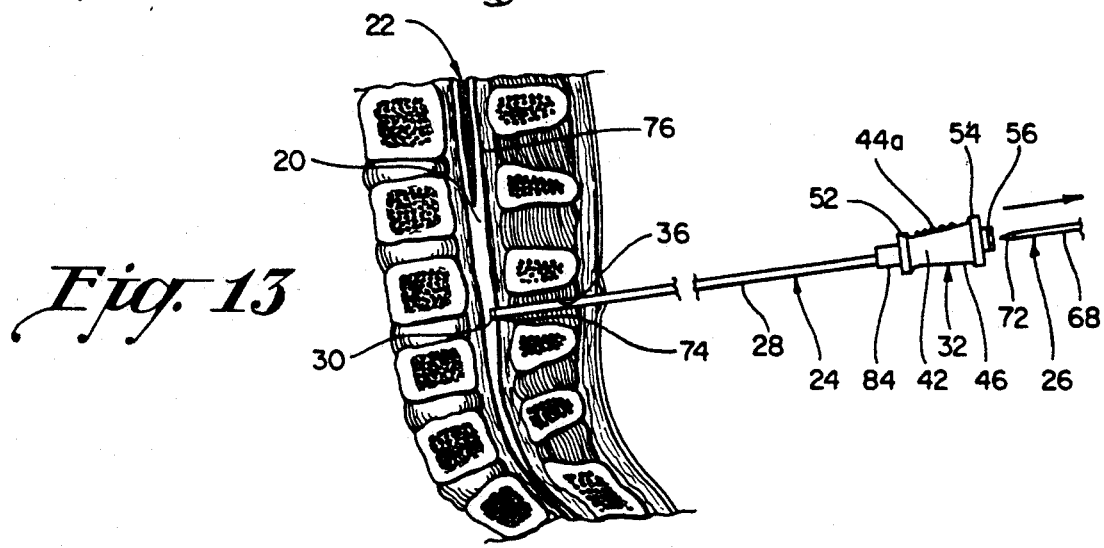
FIG. 13 is a diagrammatic view of the next step in applicants' new and improved procedure during which the stylet is withdrawn from the cannula after formation of the opening in the patient's dura.

As best illustrated in FIG. 10, the needle system 16 has a cannula 24 and a stylet 26 which are interfitted together when the procedure of the invention is initiated (FIGS. 1 and 12). The cannula 24, which is shown separately in FIGS. 2-5 and 9, is characterized by an elongated tubular member 28 having a non-pointed but beveled distal end 30 with a hub 32 provided on the opposite proximal end 34 thereof. Preferably, the elongated member 28 is formed of a smooth, inert thermoplastic, such as Teflon, which has a greater self-lubricating property than a material, such as steel, upon insertion of the elongated member 28 into a previously formed elongated puncture-like epidural passage 36 formed in a patient's back by a known-type introducer (not shown) and terminating adjacent a dura 76 which surrounds the patient's spinal cord 22 at a position along the length thereof where it has been determined by medical experts that placement of the spinal catheter 18 therethrough would be most effective for continuous administration of anesthetics and/or analgesic medications prior to and/or during and/or after various procedures. The hub 32, which is preferably formed of a plastic which is as nearly "glass-clear" as possible for a purpose which will be discussed hereinafter, is provided with a luer-tapered bore 38 (FIG. 9) which is axially aligned and in fluid communication with the proximal end 34 of the elongated member 28 mounted in the hub 32 through an axial passage 40 extending therebetween. The hub 32 is characterized by a gripping portion 42 having upper and lower curved surfaces 44 and 46, respectively, provided with transverse ridges 44a and 46a for gripping purposes and having front and rear curved surfaces 48 and 50, respectively, with viewing-window depressions 48a and 50a provided adjacent both the proximal hub-mounted end 34 of the elongated member 28 and the axial passage 40, the purpose for which will be discussed hereinafter. The gripping portion 42 has a generally rectangular flange formation 52 at its end adjacent the cannula 24 and a generally rectangular flange formation 54 at its opposite end. Projecting coaxially from the flange formation 54 is a sleeve member 56 which defines an extension of the luer-tapered bore 38 in the hub 32 and which has a generally rectangular flange 58 provided on the end thereof for a purpose which will be discussed hereinafter.

The stylet 26, as illustrated in FIGS. 6,7,8,10 and 11, is characterized by a generally rectangular, open-topped box-like handle 60 which is preferably molded of plastic. As viewed in FIGS. 6,7 and 10, the handle 60 is shown on its side with its open top facing toward the left. The handle 60 is characterized by a bottom wall 62 and four side walls 64, all of which flare slightly outwardly from the bottom wall 62. A generally cylindrical post 66 is formed integrally on the inner surface of the bottom wall 62, in centered relationship thereon, and extends outwardly thereof beyond the edges of the side walls 64 and has a relatively stiff length of thin stylet wire 68 axially mounted, at its proximal end, in the post 66. The post 66 is provided with a luer-taper whereby when the stylet 26 is inserted into or assembled to the cannula 24, the stylet wire 68 passes into the bore 38 of the hub 32, through the axial passage 40, and into the proximal end 34 of the cannula 24 with the luer-taper post 66 being tightly received within the luer-tapered bore 38. The sleeve 56, during the foregoing assembly, enters the annular space defined between the post 66 and the side walls 64 with the fit being such that the outer end surface of the flange 58 engages the inner surface of the bottom wall 62 of the handle 60 and the outer edges of the side walls 64 engage the outer end surface of the flange formation 54, to stabilize the assembly thereof. The diameter of the stylet wire 68 is such that it freely passes through the axial passage 40 in the hub 32 and through the bore of the cannula 24. Preferably the inner end of the bore 38 is funnel-shaped, as at 70 in FIG. 9, to facilitate insertion of the stylet 26 into the cannula 24. The relative lengths of the stylet 26 and the cannula 24 is such that when fully assembled, as described, only a distal pointed end 72 of the stylet wire 68 extends just slightly beyond the beveled distal end 30 of the cannula 24, as best illustrated in FIGS. 10 and 11. The stylet pointed end 72, as best shown in FIG. 11, is provided with a pencil-point or cone-shaped configuration to minimize the size of a spinal catheter opening 74 (FIG. 13) made in a patient's dura 76 and thus minimize the loss of cerebrospinal fluid from the subarachnoid space 20, the less fluid lost the less severe the spinal headache suffered by the patient. It is noted that preferably the beveled distal end of the cannula 24 is formed to blend smoothly with the pointed end 72 of the stylet 26.

With reference to FIGS. 2,4, 6-8, and 10, interengageable means may be provided on the cannula hub 32 and the stylet handle 60. A notch 78 (FIGS. 2 and 4) may be provided on the hub flange 54 with a complementary tab (FIGS. 6,7,8 and 10) being formed on the leading edge of one of the side walls 64a of the stylet handle 60. The notch 78 and tab 80 are preferably configured to provide a known-type detent action therebetween for retaining the cannula 24 and stylet 26 in fully assembled relationship until such time that it is desired to withdraw the stylet 26 from the cannula. The handle sidewall 64a may have a raised arrow 82 molded thereon which points to the tab 80.

A secondary hub 84 having circumferentially spaced longitudinally disposed gripping ribs 86 is preferably provided on the cannula end of the hub 32 (FIGS. 2,3,5,9 and 10) for receiving the open end of a plastic needle guard (not shown).

The new and improved procedure for placing the distal end of the spinal catheter 18 through the dura 76 and into the subarachnoid space 20 with a minimal loss of cerebrospinal fluid and thus a minimization of the severity of spinal headaches suffered by patients permits the continuous or selectively spaced administration of anesthetics and/or analgesic medications without multiple intrusions through the dura 76. After an initial passage or puncture has been made by a known-type introducer, the new and improved needle system 16, comprising the stylet 26 assembled in the smooth, plastic cannula 24, is inserted into the initially formed passage with the pencil-point end 72 of the stylet 26 and the beveled end 30 of the cannula 24 forming a minimal size opening 74 in the dura 76 (FIG. 12) by spreading apart the fiber of the dura 76 rather than severing same, as occurs when stylets having wedge-shaped pointed ends are used for this purpose. It is noted that the dura openings 74 formed primarily by applicants' pencil-point stylet 26 tend to heal more rapidly than those formed by such wedge-shaped pointed ends.

Figure 14:
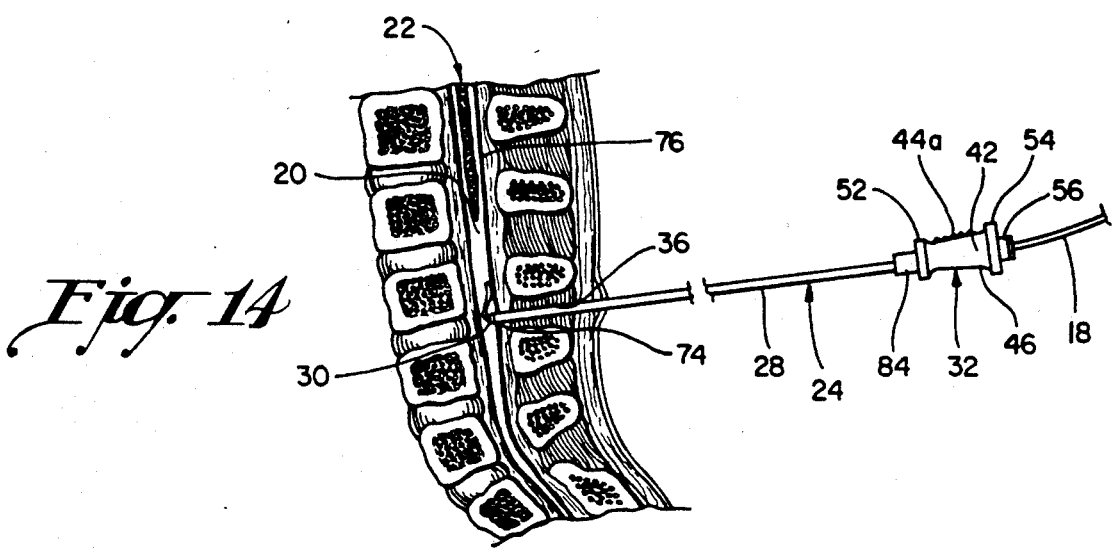
FIG. 14 is a diagrammatic view of the next step in applicants' new and improved procedure during which the distal end of a spinal catheter is introduced into the patient's subarachnoid space through the cannula which extends through the opening formed in the patient's dura, the cannula being removable from the patient after the above-described proper positioning of the spinal catheter, after which removal the spinal catheter may be suitably anchored to the patient and an appropriate drug delivery system assembled to the proximal end thereof.

After the dura opening 74 has been formed by the needle assembly 16, the stylet 26 is removed from the cannula 24 (FIG. 13), after which confirmation that the subarachnoid space 20 has been reached may be accomplished by aspirating spinal fluid through the cannula 24, the viewing recesses or depressions 48a in the cannula hub 32 permitting a visual indication and confirmation of the presence of spinal fluid in the axial passage 40 of the cannula hub 32, same being formed of a "glass-clear" plastic. Then, the spinal catheter 18 is inserted through the cannula 24 which is still disposed in the dura opening 74 and into the subarachnoid space 20 (FIG. 14). The cannula 24 may then be removed from the patient and the spinal catheter 18 anchored to the patient in a suitable manner.

Preferably the stylet 26 and the spinal catheter 18 should be of the smallest diameter possible, such as a 22 gauge stylet needle and a 24 gauge spinal catheter. Further, the spinal catheter 18 should fit as snugly as possible in the dura opening 74 so as to minimize the leakage of spinal fluid therepast.

While there has been shown and described preferred embodiments of the needle system and the procedure of the invention, it will be obvious to those skilled in the art that changes and modifications may be made without departing from the invention, and it is intended by the appended claims to cover all such changes and modifications as fall within the same spirit and scope of this invention.

We claim:

1. A needle system for introducing a spinal catheter into the subarachnoid space surrounding a spinal cord with a minimal loss of cerebrospinal fluid, said system comprising, a plastic cannula having a centrally bored hub provided at one end thereof, an elongated stylet having a cone-shaped pencil-point end and a handle at its opposite end, which stylet is insertable into said cannula through said hub, the relative lengths of said cannula and said stylet being such that, when said stylet handle abuts against said cannula hub upon full assembly thereof, said pencil-point end of said stylet projects beyond the end of said cannula whereby a minimal opening is formed in the dura by said pencil-point end of said stylet to minimize the loss of cerebrospinal fluid therethrough during removal of said stylet and insertion of a spinal catheter into the subarachnoid space through said cannula wherein said stylet is formed of stainless steel, and said cannula hub is formed of glass-clear plastic and is provided with indicator means.

2. A needle system for introducing a spinal catheter into the subarachnoid space surrounding a spinal cord with a minimal loss of cerebrospinal fluid, said system comprising, a non-pointed but beveled cannula having a hub provided at one end thereof, a bore extending through said hub in axial alignment with a bore of said cannula, an elongated stylet having a cone-shaped pointed end and a handle at its opposite end, which stylet is insertable into said cannula through said hub, the relative lengths of said cannula and said stylet being such that, when said stylet handle abuts against said cannula hub upon full assembly thereof, said cone-shaped pointed end of said stylet projects beyond the end of said non-pointed but beveled cannula whereby, when said fully assembled cannula and stylet are inserted into a previously formed elongated puncture in a patient's back, said cone-shaped pointed end of said stylet and said beveled end of said cannula pierce the dura just enough to form a minimal opening into the subarachnoid space within the dura, whereupon removal of said stylet from said cannula permits introduction of a spinal catheter through said cannula and into said subarachnoid space with a minimal loss of cerebrospinal fluid therefrom wherein said stylet is formed of stainless steel, said handle is formed of plastic, said hub is formed of glass-clear plastic and is provided with one or more viewing-window depressions.

* * * * *